(12) United States Patent
Vann et al.

(10) Patent No.: US 6,440,217 B2
(45) Date of Patent: Aug. 27, 2002

(54) APPARATUS AND METHOD FOR SPOTTING A SUBSTRATE

(75) Inventors: Charles S. Vann, Fremont; Zbigniew Bryning, Campbell, both of CA (US)

(73) Assignee: PE Corporation (NY), Foster City, CA (US)

(*) Notice: Subject to any disclaimer, the term of this patent is extended or adjusted under 35 U.S.C. 154(b) by 0 days.

(21) Appl. No.: 09/812,643

(22) Filed: Mar. 20, 2001

Related U.S. Application Data

(62) Division of application No. 09/270,218, filed on Mar. 15, 1999, now Pat. No. 6,296,702.

(51) Int. Cl.$^7$ ................................................ B05C 5/00
(52) U.S. Cl. ...................... 118/401; 118/411; 118/412
(58) Field of Search ............................... 118/401, 407, 118/410, 411, 412; 222/420

(56) References Cited

U.S. PATENT DOCUMENTS

| | | | |
|---|---|---|---|
| 2,643,801 A | | 6/1953 | Kollmeyer |
| 3,164,304 A | | 1/1965 | Jager et al. |
| 3,329,964 A | | 7/1967 | Mutschler et al. |
| 3,334,354 A | | 8/1967 | Mutschler |
| 3,843,053 A | * | 10/1974 | Thoden ................. 239/11 |
| 4,023,716 A | | 5/1977 | Shapiro |
| 4,133,918 A | | 1/1979 | Simms et al. |
| 4,155,229 A | | 5/1979 | Mitter |
| 4,165,646 A | | 8/1979 | Shapiro |
| 4,351,799 A | | 9/1982 | Gross et al. |
| 4,387,384 A | * | 6/1983 | Sue ..................... 346/140 R |

(List continued on next page.)

FOREIGN PATENT DOCUMENTS

| | | |
|---|---|---|
| DE | 19712195 | 9/1998 |
| WO | WO 89/10192 | 11/1989 |
| WO | WO 95/35505 | 12/1995 |
| WO | WO 97/44134 | 11/1997 |

OTHER PUBLICATIONS

Castellino, A.M., "When the Chips are Down," Genome Research 7:943–946 (1997).
Editorial, "Getting hip to the chip," Nature Genetics 18 (3):195–197 (1998).
Flowers, P. et al., "An Improved System for Making DNA Microarrays," www.geneticmicro.com, Poster presented at $2^{nd}$ Workshop on Methods and Applications of DNA Microarray Technology, Jan. 11–13, 1998, Tucson, AZ., pp. 1–9.
Flowers, P. et al., "DNA Microarrays Created with a Novel Instrument Designed for Use by Individual Investigators," www.geneticmicro.com, Poster presented at HGM 98, Mar. 28–30, 1998, Turin, Italy, pp. 1–8.
Fodor, S.P.A., et al., "Light–directed Spatially Addressable Parallel Chemical Synthesis," Science 251:767–773 (1991).
International Search Report from PCT/US00/06721.
Lemmo, A.V., et al., "Characterization of an Inkjet Chemical Microdispenser for Combinatorial Library Synthesis," Analytical Chemistry 69 (4):543–551 (1997).
Rose, S.S., "Application of a Novel Microarraying System in Genomics Research and Drug Recovery," Journal of the Association for Laboratory Automation 3(3):53–56 (1998).

*Primary Examiner*—James Sells
(74) *Attorney, Agent, or Firm*—Jeffrey D. Frazier

(57) ABSTRACT

The present invention provides a method and apparatus for dispensing a small volume of a selected liquid, such as a biological sample or reagent, onto a substrate. The device includes a tube adapted to contain the liquid. An elongate fiber is disposed within the tube for axial movement therein between raised and lowered positions. Upon shifting or oscillating the fiber between its raised and lowered positions, a liquid spot can be formed at a selected position on the substrate. The device is readily adaptable for the production of micro-arrays having a great number of individual spots.

6 Claims, 6 Drawing Sheets

U.S. PATENT DOCUMENTS

| | | |
|---|---|---|
| 4,400,708 A | 8/1983 | Sachs |
| 4,681,742 A * | 7/1987 | Johnson et al. ............. 422/102 |
| 4,699,884 A | 10/1987 | Noss et al. |
| 4,952,518 A * | 8/1990 | Johnson et al. ............. 436/518 |
| 4,992,729 A | 2/1991 | Nadeau |
| 5,011,779 A * | 4/1991 | Maimon .................... 435/293 |
| 5,046,539 A | 9/1991 | MacLeish et al. |
| 5,204,268 A | 4/1993 | Matsumoto |
| 5,443,791 A | 8/1995 | Cathcart et al. |
| 5,445,934 A | 8/1995 | Fodor et al. |
| 5,460,782 A | 10/1995 | Coleman et al. |
| 5,508,200 A * | 4/1996 | Tiffany et al. ................ 436/44 |
| 5,525,515 A | 6/1996 | Blattner |
| 5,540,889 A | 7/1996 | Gordon et al. |
| 5,551,487 A | 9/1996 | Gordon et al. |
| 5,574,594 A | 11/1996 | Fowler et al. |
| 5,587,522 A | 12/1996 | Selby |
| 5,601,980 A | 2/1997 | Gordon et al. |
| 5,677,195 A | 10/1997 | Winkler et al. |
| 5,756,050 A | 5/1998 | Ershow et al. |
| 5,770,151 A | 6/1998 | Roach et al. |
| 5,770,860 A | 6/1998 | Franzen |
| 5,772,966 A | 6/1998 | Maracas et al. |
| 5,807,522 A * | 9/1998 | Brown et al. ................. 422/50 |
| 5,840,256 A | 11/1998 | Demers et al. |
| 5,846,396 A | 12/1998 | Zanzucchi et al. |
| 5,849,598 A | 12/1998 | Wilson et al. |

\* cited by examiner

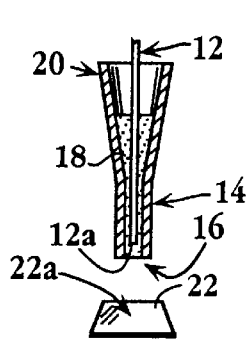
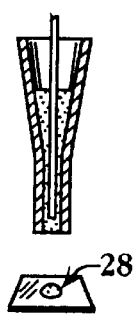
Fig. 4A    Fig. 4B    Fig. 4C
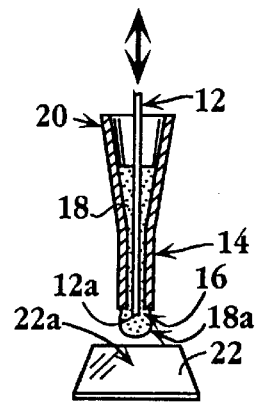
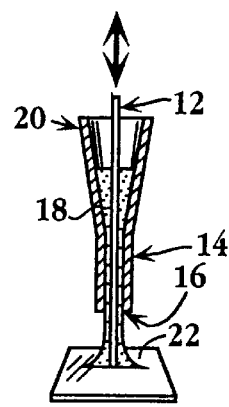
Fig. 5    Fig. 6
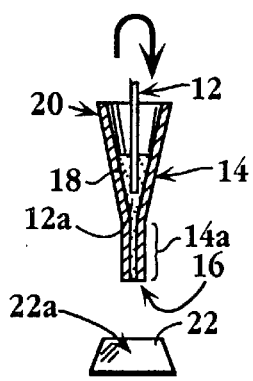
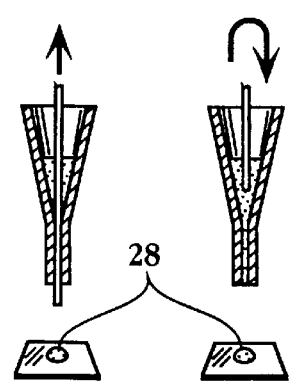
Fig. 7A    Fig. 7B    Fig. 7C    Fig. 7D    Fig. 7E

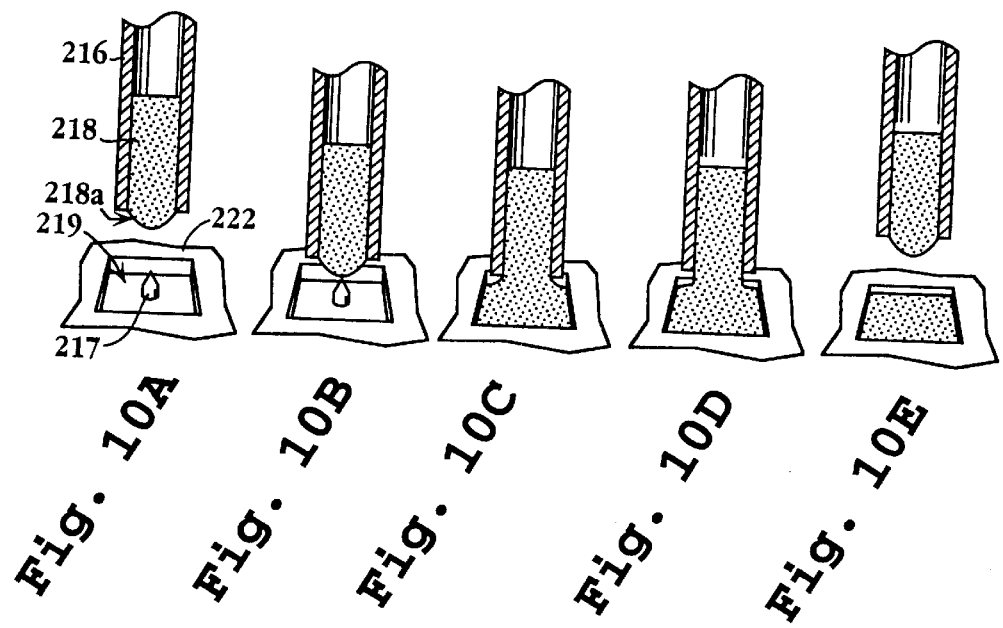
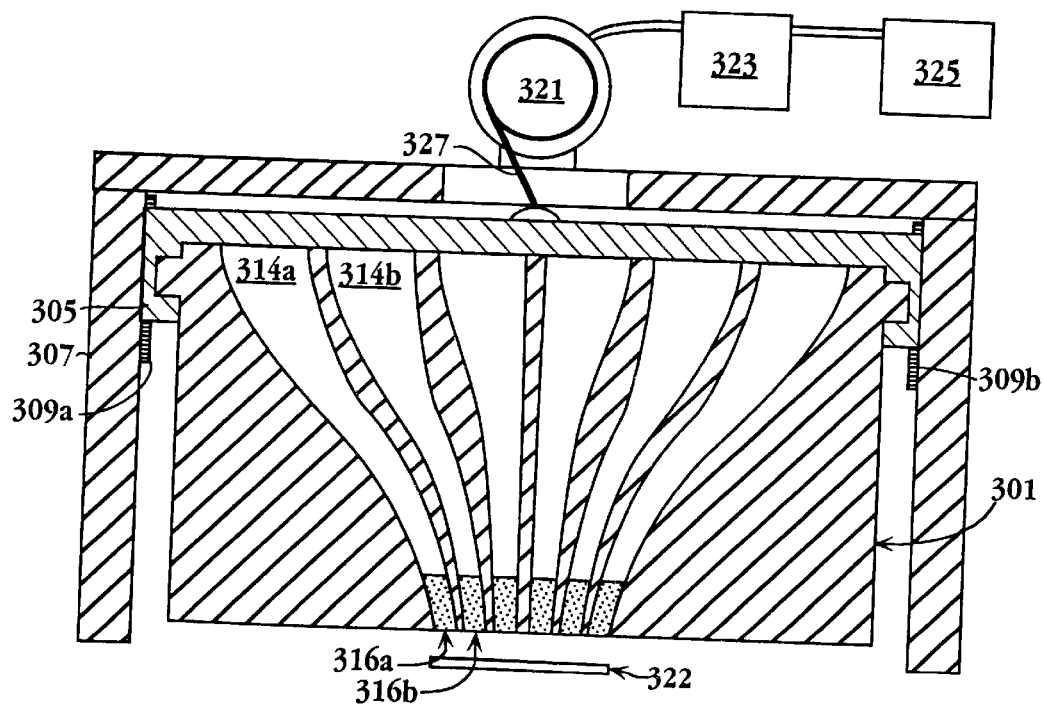

APPARATUS AND METHOD FOR SPOTTING A SUBSTRATE

CROSS REFERENCE TO RELATED APPLICATION

This application is a divisional of application Ser. No. 09/270,218, filed Mar. 15, 1999, U.S. Pat. No. 6,296,702 which is incorporated herein by reference.

FIELD OF THE INVENTION

The present invention relates to the dispensing of liquids. More particularly, the invention provides an apparatus and method of use for spotting liquids, such as biological samples or reagents, onto a substrate.

BACKGROUND OF THE INVENTION

Target compounds, or analytes, present within a sample can often be identified through the controlled exposure of the sample to an appropriate probe, with subsequent detection of a resulting reaction. In a typical arrangement, a sample of a test solution containing an analyte of interest is exposed to a probe carrying a detectable reporter. The probe is chosen such that it can specifically bind the analyte, e.g., by hybridization of complementary nucleotide sequences, or antibody-antigen interactions. After excess probe material has been removed, e.g., washed away, specific binding of the probe to the analyte can be detected.

As the sensitivity of analytical techniques continues to improve, it is increasingly desirable to carry out such analyses using very small volumes of samples/reagents. This is especially true in situations involving expensive compounds. Accordingly, it is now popular to utilize very small volumes of such liquids laid down as "spots" on the surface of a substrate, such as a slide, microcard, or chip.

Not only is it often desirable to provide ultra-small volumes of individual samples and/or reagents in the form of spots, it is becoming increasingly popular to arrange numerous such spots in close proximity to one another as an array on a substrate. For example, a lab technician might need to evaluate a specimen for the presence of a wide assortment of target biological and/or chemical compounds, or to determine the reaction of many different specimens against one or more reagents, such as labeled probes. High-density array formats permit many reactions to be carried out in a substantially simultaneous fashion, saving space, time and money.

Both manual and automated devices for dispensing very small fluid volumes have been devised, including, for example, micropipettes, pins, quills and ink-jetting devices. While suitable for some purposes, each of these is associated with certain disadvantages. For example, micropipettes are generally incapable of accurately dispensing the extremely small volumes of liquid called for by many present-day protocols. With regard to pens and quills, a number of problems need to be resolved relating to the differences in size and shape of the spots which are placed (which can lead to differences in resulting signal intensity or overlap of spots), "missed spots" (where little or no sample is placed on the surface), and the overhead associated with cleaning and reloading. Ink-jet devices dispense a controlled volume of liquid onto a substrate by use of a pressure wave created within the cartridge. This approach is not acceptable for the spotting of samples containing relatively fragile macromolecules, as they can become sheered or otherwise damaged. Further, ink-jetting devices are associated with a high degree of splattering, thereby presenting a substantial risk of contamination, particularly for closely spaced spots.

As an additional disadvantage, most of the known spotting devices require very precise placement of the spotting head relative to the substrate surface. Variations in the distance between the spotting head and the substrate surface can result in inconsistent spot sizes and/or missed spots. With particular regard to contact-type devices, if placed to close to the substrate, the spotting tip can collide with the substrate surface with a force sufficient to damage the spotting tip and/or the substrate.

In view of the above, the need is apparent for a device and method useful for delivering a micro-volume of liquid onto a substrate in a quick and precise manner. Preferably, the device should be relatively easy to use, cost effective and readily adaptable for the production of micro-arrays having a great number of individual spots.

SUMMARY OF THE INVENTION

In one of its aspects, the present invention provides an apparatus for micro-spotting a predetermined volume of a liquid at a plurality of spaced regions on a substrate or substrates.

In one embodiment, the apparatus includes a tube adapted to contain a selected liquid, such as a biological sample, reagent, or the like. The lower end of the tube defines an orifice having a diameter of less than about 1 mm. In an exemplary construction, the diameter of the orifice is less than about 500 $\mu$m, and preferably less than about 200 $\mu$m. An elongate fiber is disposed within the tube for axial movement therein between raised and lowered positions. The fiber, which has a free distal end, is provided with a diameter that is less than the inner diameter of the tube's lower end. In one exemplary arrangement, the diameter of the fiber is between about 10–100 $\mu$m smaller than that of the orifice. For example, a fiber having a diameter of about 100 $\mu$m can be disposed within a tube having an inner diameter of between about 110 to 200 $\mu$m. A workpiece holder can be employed to hold a selected substrate or substrates for spotting. At its raised position, the fiber's free end is spaced from the surface of such a substrate. At its lowered position, the fiber's free end contacts the surface of the substrate.

Shifting means are operatively connected to the fiber for shifting the same between its raised and lowered positions. The shifting means can be, for example, an actuator, such as a linear or vertical actuator, or the like. Positioning means are provided for positioning the tube and associated fiber laterally with respect to the workpiece holder, at selected deposition positions with respect to the substrate. The positioning means can be adapted to move the substrate and/or the tube, fiber and shifting means. In one embodiment, for example, the positioning means is an x-y positioner (e.g., a robotically controlled x-y movable arm) operatively connected to the tube and the shifting means.

A control unit is operatively connected to the positioning means and shifting means for use in successively (i) positioning the tube and associated fiber at a selected deposition position with respect to a substrate, and (i) shifting the fiber to its lowered position, to deposit a selected volume of liquid upon such substrate. In a preferred embodiment, the fiber is (i) laterally flexible and (ii) substantially incompressible along its longitudinal axis. Suitable fibers having such characteristics include, for example, optical fibers. Advantageously, these characteristics permit efficient transfer of motion from the shifting means to the fiber, and the accommodation of variations in the distance between the tube's lower end and the substrate by flexing, or bowing, of the fiber.

According to one embodiment, the apparatus is adapted for use in micro-spotting a predetermined volume of a liquid at a preselected position on each of a plurality of different substrates in the workpiece holder. The control unit, in this embodiment, is operable to position the tube successively at such preselected position on each substrate.

In one embodiment, the tube has a substantially uniform diameter, and includes a larger-diameter upper reservoir for holding the selected liquid. The tube and reservoir can be separately formed and subsequently attached together, or they can be integrally formed.

In another embodiment, the tube's inner diameter tapers on progressing downwardly to a defined-volume tube end region having the diameter of the orifice. The diameter of the tube end region, in this embodiment, is substantially the same as that of the fiber. The fiber's end, with such in its raised position, is disposed above the tube end region, such that shifting of the fiber from its raised to its lowered position is effective to expel from the tube the volume of liquid contained in the tube end region.

One embodiment of the apparatus, particularly useful in micro-spotting a predetermined volume of one or more selected liquids simultaneously at selected deposition regions on a substrate, includes a plurality of tubes, and associated fibers, and shifting means. The tubes can take the form, for example, of channels provided in a manifold. Fiber flexing accommodates variations in the distance between the tubes' lower ends and the associated positions at the substrate.

The present invention further provides an apparatus for micro-spotting a predetermined volume of a selected liquid on a substrate, including a tube having an inner diameter that tapers on progressing downwardly to a defined-volume tube end region having a substantially uniform diameter of less than about 1 mm. According to one embodiment, the diameter along the tube end region is less than about 500 $\mu$m, and preferably less than about 200 $\mu$m. The tube is adapted to contain the selected liquid by capillary or surface tension forces. An elongate fiber having a diameter substantially the same as that of the tube end region is disposed within the tube for axial movement therein between raised and lowered positions at which the fibers free end is disposed above and below the tube end region, respectively. Shifting means (e.g., an actuator, such as a linear or vertical actuator, or the like) are operatively connected to the fiber for shifting the same between its raised and lowered positions, whereby a defined volume of liquid contained in the tube end region is expelled from the tube onto a selected substrate disposed below the tube.

In a preferred embodiment, the fiber is (i) laterally flexible and (ii) substantially incompressible along its longitudinal axis. For example, the fiber can be an optical fiber. Advantageously, these characteristics permit efficient transfer of motion from the shifting means to the fiber, and the accommodation of variations in the distance between the tube's lower end and the substrate by flexing, or bowing, of the fiber.

According to one embodiment, the fiber makes contact with the substrate when shifted to its lowered position. In another embodiment, the fiber remains spaced apart from the substrate when shifted to its lowered position.

The micro-spotting apparatus can be used to micro-spot a predetermined volume of a liquid at a preselected position at each of a plurality of substrates. In one such embodiment, the apparatus further includes positioning means for positioning the tube and associated fiber successively at the preselected position. Fiber flexing accommodates variations in the distance between the tube's lower end and the different substrate positions.

In another embodiment, the apparatus is adapted for use in micro-spotting a predetermined volume of one or more selected liquids simultaneously at multiple selected deposition regions on a substrate. In this embodiment, the apparatus further includes a plurality of tubes, and associated fibers and shifting means. In an exemplary arrangement, the tube end regions have diameters of less than about 200 $\mu$m, the fibers are flexible fibers, and the fibers in their lowered positions are adapted to make contact with the substrate. Additionally, fiber flexing accommodates variations in the distance between the tubes' lower ends and the associated positions on the substrate.

Another aspect of the present invention provides an apparatus for producing an array of liquid-reagent spots on a substrate.

In one embodiment, the array-producing apparatus includes a manifold, or channel assembly, having a plurality of capillary channels, each adapted to hold a selected liquid. The channels have opposite upper-end and lower-end openings, and inner diameters that decrease on progressing from the upper- to the lower-end openings. The lower-end openings, in this embodiment, define the pattern and center-to-center spacing, or pitch, of the spot array. A support is movable between raised and lowered positions with respect to the manifold. A plurality of fibers are suspended from the support for movement therewith. Each fiber is adapted to move longitudinally within an associated channel, as the support is moved between its raised and lowered positions. Movement of the fibers from their raised to lowered positions is effective to deposit a selected volume of liquid from each channel in the manifold.

One embodiment further provides shifting means operatively connected to the support for shifting the same between its raised and lowered positions.

The spacing between adjacent upper-end openings of the manifold can be the same as that between adjacent lower end openings, or it can differ. In one embodiment, the spacing between adjacent upper-end openings is substantially greater than that between adjacent lower-end openings. For example, the spacing between lower-end openings can be one half, one third, or one fourth that of the upper-end openings.

According to one embodiment, the fibers are adapted to contact an underlying substrate, with the support in its lowered position, and variations in the length of fiber extending between its associated channel end and its point of contact on the substrate is accommodated by fiber flexing.

In one particular construction, the diameter of the channels at their lower ends is less than about 200 $\mu$m, and between about 10–100 $\mu$m larger than that of an associated fiber.

In another exemplary construction, each channel has a substantially uniform diameter extending along a lower end region that terminates at the channel's lower end. Further, the diameter of each channel end region is substantially the same as that of the associated fiber. The fiber's end, with such in its raised position, is disposed above the channel end region, such that shifting of the fiber from its raised to its lowered position is effective to expel from the channel the volume of liquid contained in the channel end region.

A further aspect of the present invention provides a valving apparatus for use in metering a selected amount of liquid onto the surface of a substrate.

According to one embodiment, the valving apparatus of the invention includes a reservoir for holding a selected liquid. A tube extends from the reservoir and terminates at a lower end orifice adjacent a plane adapted to be occupied by the surface of a selected substrate. A fiber is disposed in the tube for axial oscillatory movement therein, with a lower portion of the fiber extending through the orifice. The inner diameter of the tube and the diameter of the fiber are dimensioned to prevent fluid flow through the orifice in the absence of fiber oscillation. Oscillating means (e.g., an oscillating unit) operatively connect to the fiber for oscillating the same, including a control unit for determining the oscillation amplitude, frequency and time applied to the fiber, and thereby the amount of liquid allowed to pass through the tube orifice.

One embodiment of the valving apparatus further includes positioning means for positioning the tube and fiber with respect to the substrate, from one selected lateral position to another. In an exemplary arrangement, the positioning means is operatively connected to the tube, fiber and oscillating means.

In one embodiment, the oscillation means is adapted to produce an oscillation frequency of at least about 10 Hertz, and preferably at least about 100 Hertz. In another embodiment, the oscillation means is adapted to produce an oscillation amplitude of at least about 10 $\mu$m, and preferably at least about 100 $\mu$m.

In one exemplary construction, the tube of the valving apparatus has a lower-end diameter of less than about 100 $\mu$m, and the clearance between the fiber and tube at its lower end is less than about 25 $\mu$m.

The fiber of the valving apparatus can remain spaced apart from the selected substrate during its oscillation cycle, or it can be adapted to contact the substrate during at least a portion of its oscillation cycle. In one embodiment, for example, the fiber remains in contact with the substrate throughout its oscillation cycle.

In another of its aspects, the present invention provides a method of forming a reagent spot on a substrate. According to one embodiment, the method includes the steps of: (i) reciprocally moving an elongate, flexible fiber longitudinally within a capillary tube holding a selected liquid at a frequency and amplitude sufficient to pump a portion of the liquid out through an orifice at a lower end of the tube, thereby forming a pendent drop; and (ii) placing the pendent drop at a selected region on the substrate.

According to one general embodiment, the pendent drop is placed on the substrate by contacting the drop and/or the tip of the fiber with the selected region of the substrate In another embodiment, the pendent drop is placed on the substrate by maintaining the fiber in spaced relation over the selected region and enlarging the pendent drop until it falls under the force of gravity.

These and other features and advantages of the present invention will become clear from the following description.

BRIEF DESCRIPTION OF THE DRAWINGS

The structure and manner of operation of the invention, together with the further objects and advantages thereof, may best be understood by reference to the following description taken in conjunction with the accompanying drawings, in which:

FIGS. 4A to 4C illustrate a spotting device, and method of use, for delivering a micro-volume of liquid onto the surface of a substrate, in accordance with a further embodiment of the present invention;

FIG. 5 illustrates a non-contact delivery method for transferring a micro-volume of liquid from a tube to the surface of a substrate using a valving apparatus as taught by the present invention;

FIG. 6 illustrates a contact delivery method for transferring a micro-volume of liquid from a tube to the surface of a substrate using a valving apparatus as taught by the present invention;

FIGS. 7A to 7E illustrate a spotting device, and method of use, for delivering a micro-volume of liquid onto the surface of a substrate, according to an embodiment of the present invention;

FIGS. 10A to 10E illustrate an apparatus, and method of use, for delivering a liquid reagent from a tube into the well of a microplate, as taught by the present invention; and FIG. 11 is a partially schematic, side-elevational view of an automated system for simultaneously delivering one or more liquid reagents into a plurality of wells of a microplate.

DETAILED DESCRIPTION OF THE INVENTION

The following discussion of the preferred embodiments of the present invention is merely exemplary in nature. Accordingly, this discussion is in no way intended to limit the scope of the invention.

One aspect of the invention provides a device for dispensing a small volume of a liquid reagent on a substrate. Generally, the device includes a tube adapted to contain the liquid. An elongate fiber is disposed within the tube for axial movement therein between raised and lowered positions. Upon shifting or oscillating the fiber between its raised and lowered positions, a liquid spot can be formed at a selected position on the substrate.

Figure 1:
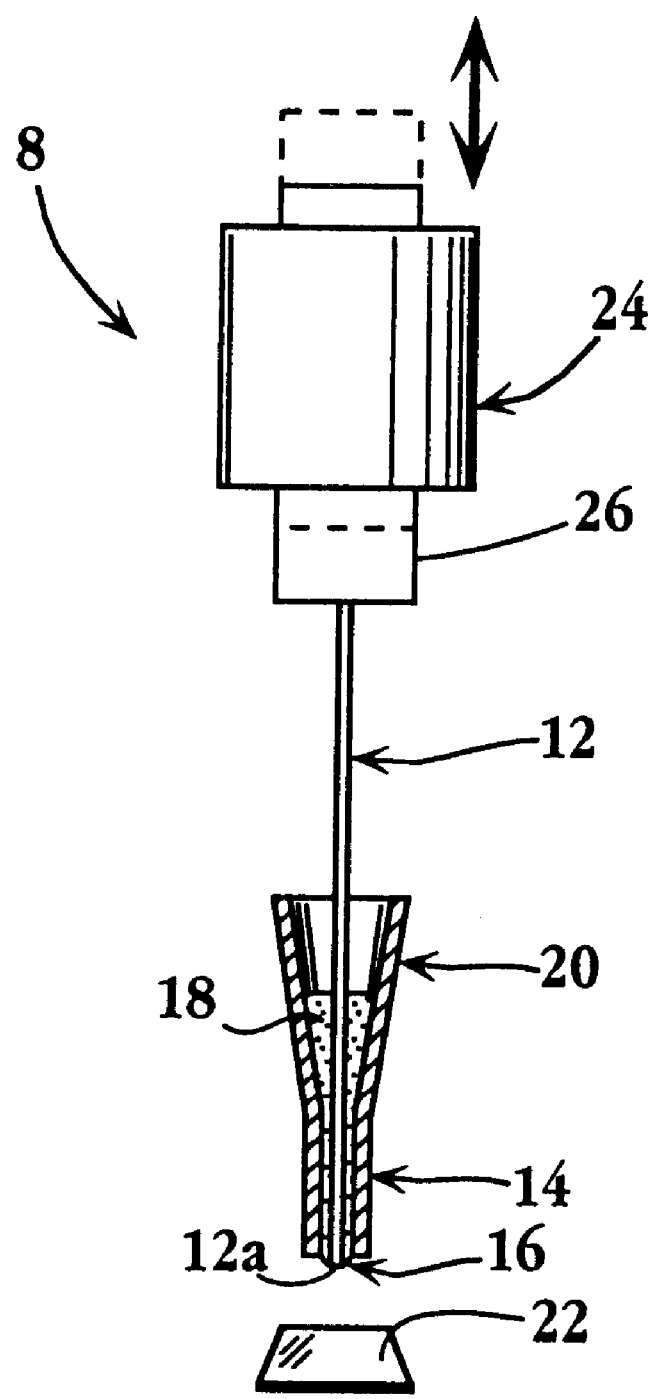
FIG. 1 is partially schematic, side-elevational view, with portions shown in section, of a spotting device constructed in accordance with an embodiment of the present invention.

In one exemplary arrangement of a spotting device, denoted generally as 8 in FIG. 1, a fiber, indicated as 12, extends longitudinally within a tube, denoted as 14, having an orifice 16 at its lower end. Tube 14 is adapted to contain a liquid reagent, such as 18, for controlled deposition on a substrate, as discussed more fully below. Tube 14 can be formed, for example, from metal, plastic, glass, ceramic, or other material(s) considered suitable by those skilled in the art. A reservoir 20, disposed in fluid communication with tube 14, is adapted to receive and hold a supply of liquid reagent. Reservoir 20 feeds liquid reagent to tube 14 as the tube's reagent content is depleted. In an exemplary construction, a hypodermic needle (gauge 30,¼ in. long, 90 deg. blunt end) is employed as the tube, and an associated plastic luer hub is used as the reservoir.

Normally, capillary or surface tension forces prevent free flow of the liquid reagent out of the tube's lower orifice. In this regard, the tube's lower region can be of capillary size, so that capillary forces prevent free flow of liquid reagent 18 out of orifice 16. For example, orifice 16, and a region of tube 14 extending upwardly therefrom, can be formed with an inner diameter of less than about 2 mm, and preferably less than about 1 mm. In one particular construction, the inner diameter along the lower region of tube 14 is less than about 200 µm. To further encourage the desired capillary action, the capillary-size region of tube 14 can be provided with an interior surface that is hydrophilic, i.e., wettable. For example, the interior surface of tube 14 can be formed of a hydrophilic material and/or treated to exhibit hydrophilic characteristics. In one embodiment, the interior surface has native, bound or covalently attached charged groups. One suitable surface is a glass surface having an absorbed layer of a polycationic polymer, such as poly-l-lysine.

Tube 14 can be provided with an exterior surface that is hydrophobic, i.e., one that causes aqueous medium deposited on the surface to bead. For example, the exterior surface of tube 14 can be formed of a hydrophobic material and/or treated to exhibit hydrophobic characteristics. This can be useful, for example, to prevent spreading of a drop, formed at the region of orifice 16, along the outer surface of the tube. It can also be useful to maintain a drop of liquid in the form of a globule at the lowermost tip. A variety of known hydrophobic polymers, such as polystyrene, polypropylene, and/or polyethylene, can be utilized to obtain the desired hydrophobic properties. In addition, or as an alternative, a variety of lubricants or other conventional hydrophobic films can be applied to the tube's exterior surface, particularly along the tube's lower region proximate outlet 16.

With continuing reference to the embodiment of FIG. 1, the diameter of fiber 12 is between about 10 to 500 µm smaller than the inner diameter of tube 14. In this regard, fiber 12 can have a diameter of between about 25 to 1,000 µm. According to one embodiment, fiber 12 has a diameter of less than about 200 µm, and preferably less than about 100 µm. in one particular arrangement, a fiber having a diameter of about 75 µm extends longitudinally within a tube having an inner diameter of about 100 µm along its lower region, and an outer diameter of about 200 µm. In another arrangement, a fiber having a diameter of about 50 µm extends longitudinally within a tube having an inner diameter of about 75 µm along its lower region, and an outer diameter of about 200 µm.

For reasons that will become apparent, fiber 12 is preferably constructed to be laterally flexible and longitudinally incompressible. Materials suitable for forming fiber 12 include those typically employed in the construction of optical fibers, such as glass, plastic, silica, quartz, and the like. Suitable optical fibers are available from a number of commercial sources. One particularly preferred fiber, having a diameter of about 0.002 inches (i.e., about 50.8 µm), is that supplied by Edmund Scientific Co. (Barrington,. N.J.) under catalog # F54014.

As previously indicated, fiber 12 is disposed within tube 14 for axial movement therein between raised and lowered positions. In the present embodiment, when in the raised position, the fiber's free end or tip 12a is spaced apart from the surface of a selected substrate, such as slide 22. When shifted to the lowered position, tip 12a approaches the surface of substrate 22.

Shifting means are operatively connected to fiber 12 for shifting the same between its raised and lowered positions. The shifting means can include, for example, an actuator that is movable between two positions, such as a linear or vertical actuator, or the like. In the embodiment of FIG. 1, for example, a solenoid assembly 24 is activatable to draw a solenoid piston 26 downwardly, then release the piston, e.g., under spring bias, to a normal, raised position (shown in dashed lines). Many solenoids are available from commercial sources, and suitable models can be readily chosen by those skilled in the art. One particular solenoid, contemplated for use herein, is available from Jameco Electronics Components (Belmont, California) under part # 145314 (12 VDC Continuous Tubular Push/Pull Solenoid). In one embodiment, the solenoid is operable to shift the fiber up and down over a stroke of about 1 mm.

Other actuators, useful for shifting the fiber, include, for example, pneumatic, hydraulic, magnetostrictive, and piezoelectric actuators, as well as motor assemblies (e.g., steppers) operable to generate a downward motive force followed by reciprocation. Several particular assemblies which can be readily adapted for use herein as the shifting means are disclosed, for example, in U.S. Pat. Nos. 3,164, 304; 3,329,964; 3,334,354; 5,443,791; 5,525,515; 5,551, 487; 5,601,980; and 5,807,522; each of which is expressly incorporated herein by reference.

Positioning means can be utilized to move the spotting device linearly or in an x-y plane to position the spotting device at a selected deposition position. In this regard, certain embodiments provide for movement of the tube while the target substrate is held stationary. According to other embodiments, the tube remains in a fixed position, while the substrate is shuttled into position. Still further embodiments provide for movement of both the tube and the target substrate, either sequentially or in parallel.

In one exemplary arrangement of the positioning means, the spotting device is carried on an arm of an x-y positioner. The arm, in this arrangement, can be moved either linearly or along an x-y plane to position the spotting device at a selected deposition position. Such movement can be accomplished, for example, using a robotic assembly, or the like. Exemplary robotic devices include, for example, robots with electronically controlled linked or crossed movable arms, such as a SCARA, gantry and Cartesian robots. It is understood, of course, that any other robotic mechanism could be used in accordance with the present invention so long as it can accomplish substantially the same purposes and secure substantially the same result. In this regard, cylindrical robots, polar robots, articulated robots, or the like can be utilized. In one embodiment, the positioning means comprises a motorized x-y carriage or rail assembly. For example, an AUTOMOVE® 402, available from Asymtek (Carlsbad, Calif.), can be used for x-y positioning and solenoid activation.

The arm that supports the tube, in the above arrangement, can include a clamp capable of releasably grasping the tube. This arrangement permits swapping of the tube with a different one, e.g., loaded with a different liquid reagent, as desired.

Figure 2:
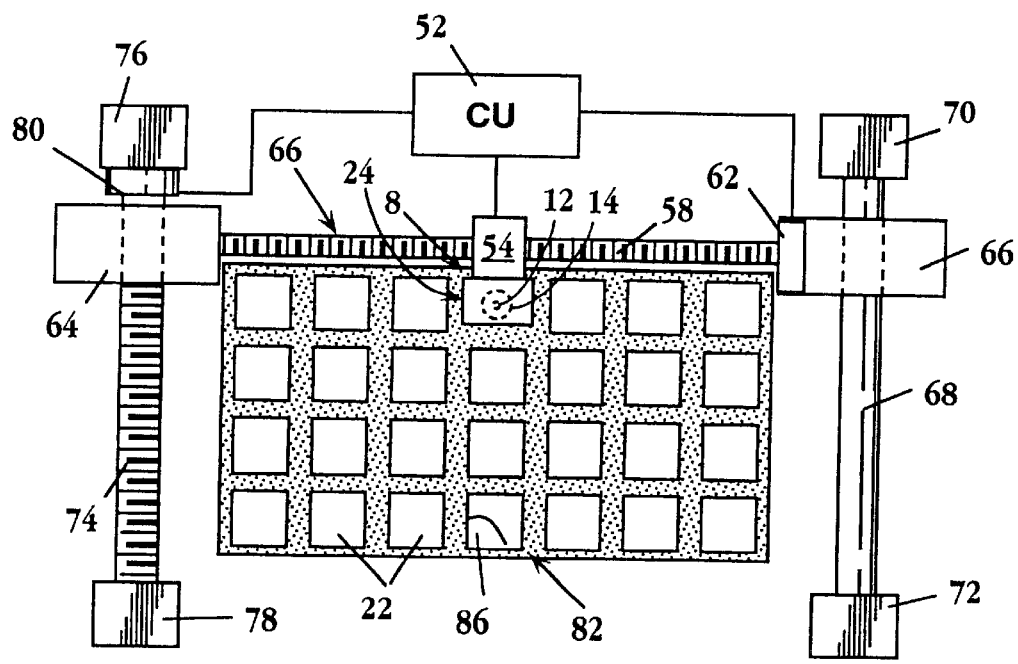
FIG. 2 is a partially schematic, top plan view showing components of an automated apparatus for forming arrays in accordance with the invention.

One particular positioning means, contemplated for use herein, will now be described in detail. The apparatus is shown in planar, and partially schematic view in FIG. 2. A spotting device 8 in the apparatus has the basic construction described above with respect to FIG. 1, and includes a tube 14 terminating at a lower orifice. A fiber 12, disposed axially within the tube 14 of the spotting device 8, is adapted for movement toward and away from the surface of a substrate, to dispense a selected volume of liquid sample or reagent, as described herein. A solenoid 24, or other shifting means, effects this movement. Solenoid 24 is under the control of a control unit 52 whose operation will be described below.

The spotting device is carried on an arm 54 that is threadedly mounted on a worm screw 58 driven (rotated) in a desired direction by a stepper motor 62 also under the control of unit 52. At its left end in the figure, screw 58 is carried in a sleeve 64 for rotation about the screw axis. At its other end, the screw is mounted to the drive shaft of the stepper motor, which in turn is carried on a sleeve 66. The spotting device, worm screw, the two sleeves mounting the worm screw, and the stepper motor used in moving the device in the "x" (horizontal) direction in the figure form what is referred to here collectively as a displacement assembly 66.

The displacement assembly is constructed to produce precise, micro-range movement in the direction of the screw, i.e., along an x axis in the figure. In one mode, the assembly functions to move the spotting device in x-axis increments having a selected distance in the range 5–500 μm. In another mode, the spotting device may be moved in precise x-axis increments of several microns or more, for positioning the spotting device at associated positions on adjacent substrates, as will be described below.

The displacement assembly, in turn, is mounted for movement in the "y" (vertical) axis of the figure, for positioning the spotting device at a selected y axis position. The structure mounting the assembly includes a fixed rod 68 mounted rigidly between a pair of frame bars 70, 72, and a worm screw 74 mounted for rotation between a pair of frame bars 76, 78. The worm screw is driven (rotated) by a stepper motor 80 that operates under the control of unit 52. The motor is mounted on bar 76, as shown.

The structure just described, including worm screw 74 and motor 80, is constructed to produce precise, micro-range movement in the direction of the screw, i.e., along a y axis in the figure. As above, the structure functions in one mode to move the spotting head in y-axis increments having a selected distance in the range 5–500 μm, and in a second mode, to move the spotting head in precise y-axis increments of several microns or more, for positioning the spotting head at associated positions on adjacent substrates.

A workpiece holder 82 in the apparatus functions to hold a plurality of substrates, such as substrates 22 on which the microarrays of reagent regions are to be formed by the apparatus. The holder provides a number of recessed slots, such as slot 86, which receive the substrates, and position them at precise selected positions with respect to the frame bars on which the spotting device positioning means is mounted.

As noted above, the control unit in the device functions to actuate the two stepper motors and solenoid in a sequence designed for automated operation of the apparatus in forming a selected microarray of reagent regions on each of a plurality of substrates.

The control unit is constructed, according to conventional microprocessor control principles, to provide appropriate signals to the solenoid and each of the stepper motors, in a given timed sequence and for an appropriate signaling time. The construction of the unit, and the settings that are selected by the user to achieve a desired array pattern, will be understood from the following description of a typical apparatus operation.

Initially, one or more substrates are placed in one or more slots in the holder. Motors 62, 80 are then actuated to position the spotting device at a selected array position at the first of the substrates. Solenoid actuation of the spotting device is then effected to dispense a selected-volume aliquot of that reagent at this location. This operation is effective, for example to dispense a selected volume preferably less than about 1 μl (e.g., between about 2 pi and 2 nl) of the liquid reagent.

The spotting device is now moved to the corresponding position at an adjacent substrate and a similar volume of the liquid reagent is dispensed at this position. The process is repeated until the reagent has been dispensed at this preselected corresponding position on each of the substrates.

Where it is desired to dispense a single reagent at more than two array positions on a substrate, the spotting device may be moved to different array positions at each substrate, before moving the spotting device to a new substrate, or liquid reagent can be dispensed at individual positions on each substrate, at one selected position, then the cycle repeated for each new array position.

To dispense the next reagent, the spotting device is exchanged for another such device containing a different selected reagent. The process of dispensing the reagent at each of the corresponding second-array positions is then carried out as above. This process is repeated until an entire microarray of liquid reagents on each of the substrates has been formed.

Several other x-y positioning assemblies which can be readily adapted for use herein as the positioning means are disclosed, for example, in U.S. Pat. Nos. 5,443,791; 5,551,487; and 5,587,522; each of which is expressly incorporated herein by reference.

As previously mentioned, the positioning means can instead, or in addition, be adapted to move the substrate to a spotting position. In this regard, the substrate can be adapted for manipulation by a robotic assembly, or it can be supported on a conveyor, or an x-y movable stage or platform.

Any desired substrate(s) can be used with the present invention, including slides, cards, plates, chips, and the like. In one general embodiment, the substrate surface is relatively hydrophilic, i.e., wettable. For example, the surface can have native, bound or covalently attached charged groups. One such surface is a glass surface having an absorbed layer of a polycationic polymer, such as poly-l-lysine. In one embodiment, for example, an aqueous or predominantly aqueous reagent solution or biological sample is spotted onto a slide having a hydrophilic surface. In another embodiment, the substrate surface has or is formed to have a relatively hydrophobic character, i.e., one that causes aqueous medium deposited on the surface to bead. A variety of known hydrophobic polymers, such as polystyrene, polypropylene, or polyethylene have desired hydrophobic properties, as do a variety of lubricant or other hydrophobic films that may be applied to the substrate surface.

In some cases, it is desired to spot out the reagents in a humid environment so that the droplets do not dry until the arraying operation is complete.

Several exemplary devices and methods for spotting a substrate are depicted in FIGS. 3 to 6. Generally, a spotting device of the invention is positioned over a selected region of a substrate. In a typical operation, this is accomplished by aligning the selected region of the substrate with the spotting device such that the selected region intersects a line defined by an extrapolation of the spotting device's central longitudinal axis. An elongated fiber adapted for movement axially within the spotting device is then shifted or oscillated between its raised and lowered positions in a manner effective to transfer an aliquot of liquid from the tube onto the selected region of the substrate. It should be noted that any of the above shifting means and positioning means can be used in connection with the following embodiments. Also, any suitable control unit, such as 52 in FIG. 2, can be employed.

It should also be noted that, as the fiber reciprocates in a cycle from its raised position to its lowered position and back, the fiber's terminal end or tip will travel through a path referred to herein as the "stroke." Along its forward stroke, the tip travels from a raised peak to a lowered peak. Along its back stroke, the tip travels from its lowered peak back to its raised peak.

Figures 3A, 3B, 3C:
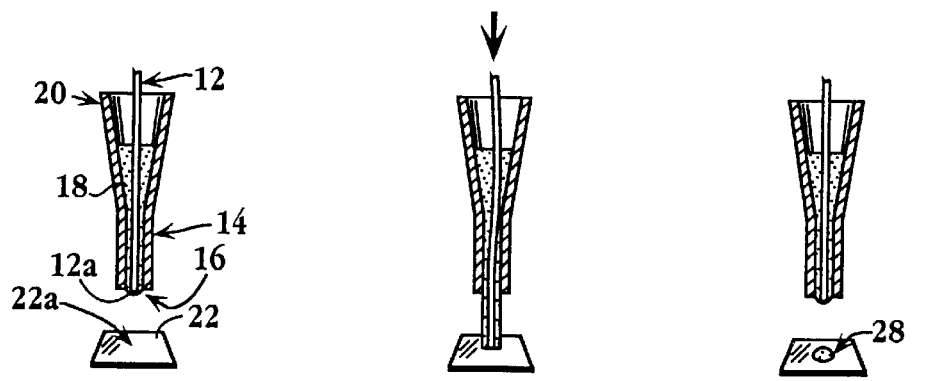
FIGS. 3A to 3C illustrate a spotting device, and method of use, for delivering a micro-volume of liquid onto the surface of a substrate, in accordance with one embodiment of the present invention.

In one embodiment, shown in FIGS. 3A to 3C, at the beginning of its stroke, i.e., at its raised peak, the tip 12a of fiber 12 is situated outside of tube 14, such that a section of fiber 12 intersects a plane defined by the terminal rim of tube 14 at orifice 16. From this beginning position, illustrated in FIG. 3A, the fiber's tip 12a is moved toward the surface of a selected substrate, such as slide 22, eventually reaching its lowered peak whereat tip 12a contacts a selected substrate region 22a, as shown in FIG. 3B. It should be noted that fiber 12 carries with it a layer of liquid reagent 18 on its exterior surface, including at the surface of tip 12a. Upon contacting the substrate, a small and controlled portion of liquid reagent is delivered from tip 12a to the selected region 22a of substrate 22. After contacting substrate 22, fiber 12 is shifted back to its raised position, leaving behind a spot of liquid, as at 28, on the substrate's surface. The spotting device can then be positioned over another selected region to lay down an additional spot, if desired. The repetition rate employed can be a few strokes per second, e.g., within the range of about 1–10 Hz. In one embodiment, the repetition rate is about 5 strokes per second.

It should be appreciated that an exacting tolerance between the spotting device and substrate is not critical to achieve successful results using the spotting device of the present invention. That is, the fiber can retreat back to its raised position after only barely touching the substrate surface, or the fiber can be lowered farther than what is necessary toward the substrate surface in order to bring its tip into contact therewith. Advantageously, the flexibility of the fiber permits the fiber to flex, or bow, once the tip abuts the substrate surface. That is, flexing of the fiber can accommodate variations in the distance between the lower end of the spotting device and the surface of the substrate. This is shown in exaggerated fashion in FIG. 3B for convenience of illustration.

It should also be appreciated that the longitudinal incompressibility of the fiber provides for the efficient transmission of motion from the shifting means to the fiber's tip. Advantageously, this property permits the use of fibers of varying lengths, including relatively long fibers (e.g., 10, 20, 30 cm, or more).

In another embodiment (not shown), similar to the embodiment just described, the forward stroke can bring the fiber's tip very close to the selected surface region of the substrate, without actually making contact. This permits liquid reagent on the fiber's terminal end to touch and adhere to the substrate surface, while actual physical contact between the tip itself and the substrate surface is avoided. While advantageous for certain purposes, it will be appreciated that this embodiment will generally be less desirable than the previously described embodiment, since an exacting tolerance between the spotting device and the substrate surface is required in this case.

Another spotting method is depicted in FIGS. 4A to 4C. Here, at the beginning of its stroke, i.e., at its raised peak, the tip 12a of fiber 12 is situated within tube 14, above the plane defined by the terminal rim of tube 14 at orifice 16. From this beginning position, illustrated in FIG. 4A, the fiber tip 12a is moved toward the surface of a selected substrate, such as slide 22. Plunger- or piston-like action of tip 12a acts to push an aliquot of liquid reagent 18 from the lower end region of tube 14. The amount of liquid pushed out in this manner will depend, in part, on the volume of liquid occupying the region under tip 12a at the time tip 12a is moved toward substrate 22. Thus, the location of the tip's raised peak within the tube, in this embodiment, will typically be determined, at least in part, by the quantity of liquid that one desires to spot on a substrate. Other variables that can be adjusted in order to control the amount of liquid deposited in this embodiment include the surface area of tip 12a, and the distance of the gap separating the fiber from the tube's interior surface.

As tip 12a is moved toward substrate through its stroke, it eventually reaches its lowered peak, in contact with substrate 22. After contacting substrate 22, fiber 12 is shifted back to its raised position, leaving behind a spot of liquid, as at 28 in FIG. 4C, on the substrate's surface. The spotting device can then be positioned over another selected region to lay down an additional spot, if desired. As with the previously described embodiment, the repetition rate employed can be a few strokes per second, e.g., within the range of about 1–10 Hz. In one embodiment, the repetition rate is about 5 strokes per second.

It should be appreciated that the piston-like action of fiber 12, as just described, causes a thicker layer of liquid to form at the fiber's lower end region, as compared to the embodiment of FIGS. 3A to 3C. Thus, it is contemplated that this embodiment will be used to create reagent spots having a greater volume.

In another embodiment (not shown), similar to the embodiment just described, the fiber's tip can be moved toward the selected surface region of the substrate, without making contact. For example, movement of the fiber tip toward the substrate can be abruptly stopped, or reversed, so that liquid is thrown or ejected, e.g., as by inertia, from the fiber onto the substrate. Or, the fiber tip can be moved into very close proximity to the substrate surface, without physically contacting it, so that liquid reagent carried on the fiber touches and adheres to the substrate.

A further aspect of the present invention provides a valving apparatus for use in metering a selected amount of liquid onto the surface of a substrate. In one embodiment, shown in FIGS. 5 and 6, a tube 14 communicates at its upper end with a reagent-supply reservoir 20, and terminates at a lower end orifice 16, much like the previously described spotting devices. A fiber 12 is disposed in tube 14 for axial oscillatory movement therein.

The inner diameter of tube 14 and the diameter of fiber 12 are dimensioned to prevent fluid flow through orifice 16 in the absence of fiber oscillation. In one embodiment, for example, tube 14 has a lower-end diameter of less than about 200 $\mu$m, and preferably less than about 100 $\mu$m, and the clearance between the fiber and tube at its lower end is less than about 50 $\mu$m, and preferably less than about 25 $\mu$m.

Oscillating means operatively connect to fiber 12 for oscillating it. The oscillating means can comprise, or example, an oscillating unit having a control unit for determining the oscillation amplitude, frequency and time applied to the fiber, and thereby the amount of liquid allowed to pass through orifice 16. The oscillating unit can comprise any device capable of oscillating the fiber axially within the tube in such a controlled manner. Suitable oscillating units can include, for example, a solenoid or motor assembly, or a pneumatic, hydraulic, magnetostrictive, or piezoelectric actuator. In one embodiment, the oscillating means is adapted to produce an oscillation frequency of at least about 10 Hz, and preferably at least about 100 Hz. Preferably, the oscillating means is adapted to produce an oscillation amplitude of at least about 10 $\mu$m, and preferably at least about 100 $\mu$m.

The valving apparatus can further include positioning means for positioning the tube and fiber with respect to the substrate, from one selected lateral position to another. In one embodiment, the positioning means is operatively connected to the tube, fiber and oscillating means. The positioning means can comprise devices as set forth above with regard to the spotting device.

In operation, fiber 12 can be moved axially within the liquid-holding tube in a reciprocal fashion. Such oscillatory movement occurs at a frequency and amplitude, and for a length of time, sufficient to pump a selected quantity of liquid reagent 18 out through orifice 16 at a lower end of tube 14, thereby forming a pendent drop, such as at 18a in FIG. 5. The pendent drop can be placed at a selected region of a substrate by contacting the drop 18a with the selected substrate region. In one embodiment, the fiber's tip 12a is moved into contact with the substrate. Such contact can be periodic, e.g., once per oscillation of the fiber, or it can be continuous such that the fiber engages the substrate throughout its oscillation cycle. It should be appreciated that formation of such a "liquid bridge," as illustrated in FIG. 6, permits the creation of relatively large reagent spots. Alternatively, the pendent drop can be placed on the substrate by maintaining the fiber in spaced relation over the selected region and enlarging the pendent drop until it falls under the force of gravity.

Another exemplary spotting device of the present invention is depicted in FIGS. 7A to 7E. Similar to the previous embodiments, a flexible fiber 12 extends longitudinally through a tube 14 having a lower orifice 16. In this embodiment, however, the inner diameter of tube 14 tapers on progressing downwardly to a defined-volume tube end region, indicated generally at 14a, having a substantially uniform diameter. Preferably, the tube end region 14a diameter is substantially the same as the diameter at orifice 16. Further, the inner diameter along the lower end region 14a of tube 14, proximate orifice 16, is very close to (e.g., within about 10 $\mu$m), and preferably substantially the same as, the diameter of fiber 12. For example, in one embodiment, both the fiber's diameter and the inner diameter of the tube, along region 14a, are less than about 200 $\mu$m; and are preferably about 100 $\mu$m. In another embodiment, both of these values are about 50 $\mu$m. The upper, larger diameter portion of the tube can act as a supply reservoir 20 for feeding liquid reagent to the lower tube portion as spotting operations are effected.

Shifting means are operatively connected to fiber 12 for shifting the fiber between its raised and lowered positions. The apparatus can further include positioning means for positioning the tube and fiber with respect to the substrate, to from one selected lateral position to another. In one embodiment, the positioning means operatively connect to the tube, fiber and oscillating means. The shifting means and the positioning means can comprise devices as previously set forth herein.

Steps of a typical operation are depicted sequentially in FIGS. 7A through 7E. Initially, the shifting means (not shown) shifts fiber 12 from its raised position, of FIG. 7A, towards a substrate, such as slide 22. Notably, when fiber 12 is in its raised position, its tip 12a is disposed above the tube end region 14a. As fiber 12 is shifted from its raised to its lowered position, the volume of liquid reagent 18 occupying the tube end region 14a is expelled from tube 14, as depicted in FIG. 7B. When fiber 12 reaches its lowered position, as shown in FIG. 7C, the expelled liquid reagent is transferred to a selected region 22a of substrate 22. As fiber 12 is shifted back to its raised position, as shown in FIGS. 7D and 7E, a spot of liquid reagent 28 is left behind on the surface of substrate 22. When the fiber is fully retracted back into the fluid container (FIG. 7E), another deposition cycle is ready to begin, if desired.

As with those previous embodiments involving contact between the fiber and the substrate, it should be appreciated that an exacting tolerance between the spotting device and substrate is not critical to achieve successful results using the just-described spotting device. Advantageously, the flexibility of the fiber permits the fiber to flex, or bow, once the tip abuts the substrate surface, as shown in exaggerated fashion in FIG. 7C for convenience of illustration. That is, flexing of the fiber can accommodate variations in the distance between the lower end of the spotting device and the surface of the substrate. It should also be appreciated that the longitudinal incompressibility of the fiber provides for the efficient transmission of motion from the shifting means to the fiber's tip.

One embodiment provides an operation substantially like that of FIGS. 7A to 7E, except that the fiber's lower tip never makes contact with the substrate surface. For example, movement of the fiber tip toward the substrate can be abruptly stopped, or reversed, so that liquid is thrown or ejected, e.g., as by inertia, from the fiber onto the substrate. Or, the fiber tip can be moved into very close proximity to the substrate surface, without physically contacting it, so that liquid reagent expelled by the fiber touches and adheres to the substrate.

Still a further aspect of the present invention provides a hand-operable spotting device (not shown). The tube, in this embodiment, is dimensioned to fit comfortably in the hand of an operator. In this regard, the outer dimensions of the hand device are preferably similar to those of typical writing implements, such as ink pens, mechanical pencils, and the like. For example, the tube can have an outer diameter of between about 0.75–1.50 cm and a length of between about 10–20 cm. An elongate, flexible fiber, e.g., an optical fiber, is disposed within the tube for axial movement therein between raised and lowered positions. The tube is adapted to hold, e.g., by way of capillary forces, a selected liquid reagent for deposition. The interior dimensions of the tube, and the dimensions of the fiber, can be as set out for any of the foregoing embodiments.

The fiber of the hand device attaches at its upper end to a piston that is adapted for reciprocal movement within the tube. Normally, the piston is urged away from a lower orifice of the tube, toward the top of the tube, by a coil spring or other biasing mechanism. At this position, the fiber is shifted toward its raised position, substantially retracted into the tube. The shifting means, in this embodiment, includes a depressible shaft having an end region that protrudes through an opening at the upper end of the tube. The other end of the shaft, located within the tube, operatively engages the piston. Upon depressing the rod, e.g., using the thumb of an operator's grasping hand, the normal biasing force of the coil spring can be overcome, so that the piston is pushed downwardly through the tube. Such movement of the piston causes the fiber to move axially within the tube, so that the fiber's lower end protrudes from the tube's lower orifice. At this position, a liquid spot can be transferred from the fiber's tip to a selected position on a substrate. Upon releasing the depressible shaft, the coil spring returns the fiber to its raised position.

In another of its aspects, the present invention provides a spotting head for producing an array of liquid-reagent spots on a substrate. As discussed more fully below, the spotting head of the invention can be adapted to lay a great number, e.g., hundreds or thousands, of spots per second.

Figure 8:
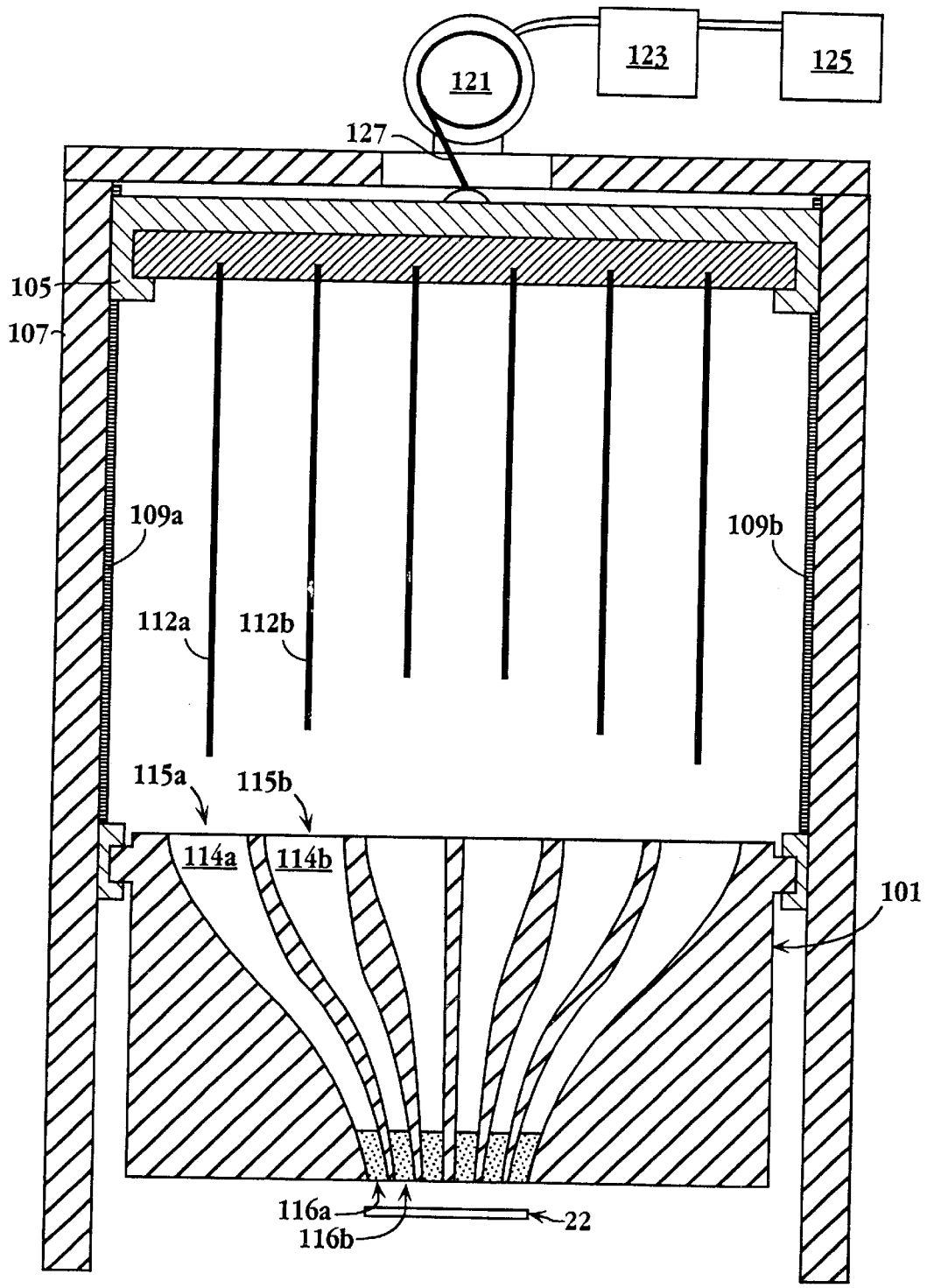
FIGS. 8 and 9 are partially schematic, side-elevational views of a spotting head for laying down an array of liquid spots on the surface of a substrate, according to an embodiment of the present invention.

One embodiment of the spotting head is shown in FIG. 8. In this embodiment, a conduit or channel assembly 101, also referred to herein as a manifold, includes a plurality of channels, such as 114a–114b. Each channel 114a, 114b has opposite upper-end and lower-end openings, as at 115a–115b and 116a–116b, respectively. The channels are maintained in fixed, spaced relation to one another. In one embodiment, the channels take the form of tubes, barrels or funnels that are secured (e.g., snap fit) into a frame or rack body. In another embodiment, the channels are of a monolithic construction. For example, the channel assembly can be integrally constructed of plastic using an injection molding process; or each channel can be formed by boring through a block of material, such as glass, plastic, metal, or the like.

The inner diameter of each channel decreases on progressing from the upper- to the lower-end openings. For example, the channels can be generally cone-shaped or horn-shaped channels. The longitudinal axis of each channel can be straight, angled, curved, or other suitable shape. In this regard, attention is directed to the generally S-shaped channels shown in FIG. 8.

A region of each channel extending from a respective one of the lower-end openings is of capillary size, such that a liquid, e.g., a biological sample or reagent solution, placed in the channel will normally be maintained therein by way of capillary forces. Any inner diameter that effects the desired capillary action can be utilized within the scope of this invention. For example, the capillary-size regions can be formed with an inner diameter of less than about 1 mm, and preferably less than about 200 $\mu$m. To further encourage the desired capillary action, the capillary-size region of each conduit can be provided with an interior surface that is hydrophilic.

While only six channels, arranged side-by-side in a linear fashion, are visible in the view of FIG. 8, it should be understood that any reasonable number of channels can be disposed in any desired spatial configuration. For example, the manifold can include 24, 48, 96, 384, 1024, 1536 channels, or more. In such arrangements, the channel upper- and lower-end openings will typically be arranged in a regular array, e.g., an 8×12, 16×24, 32×32, or a 32×48 array, though other layouts are possible.

A support, denoted as 105, is adapted for movement between raised and lowered positions with respect to manifold 101. In the embodiment of FIG. 8, this is accomplished by providing a frame, such as 107, having a track comprised of spaced-apart, parallel linear rail portions, denoted as 109a and 109b, along which support 105 is guided. For example, support 105 can have a groove or slot (not shown) formed along each of its side-end regions, proximate rails 109a, 109b, with each slot being slidably mounted over a respective one of the rails.

Figure 9:
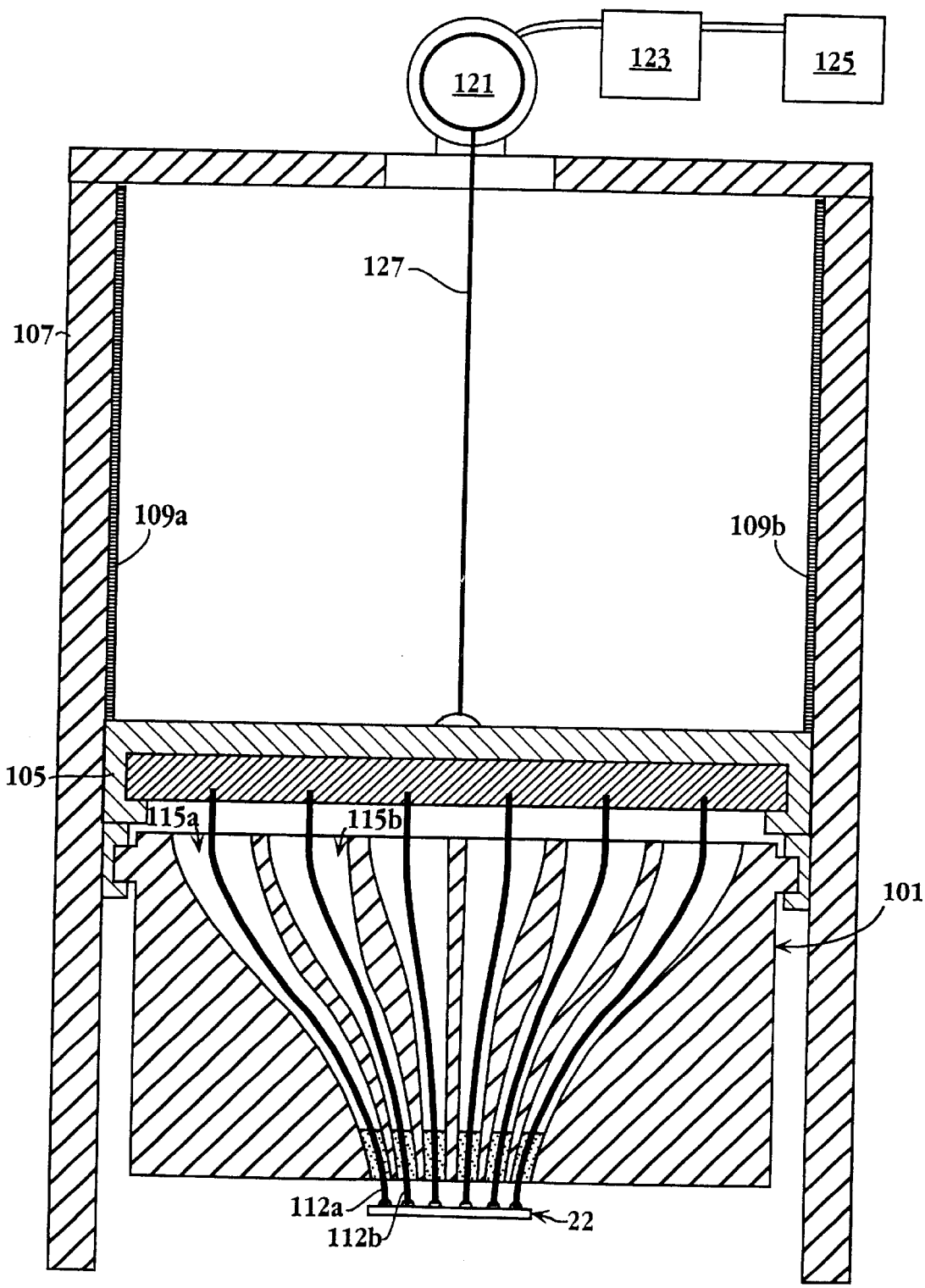

Movement and positioning of support 105 along the track can be effected by way of manual or automatic shifting means. In this regard, and with additional reference to FIG. 9, a motor assembly 121 communicates with a controller 123 and power supply 125. A flexible wire or line 127 extends between motor 121 and support 105. One end of wire 127 is connected to an upper side of support 105. The other end of wire 127 is secured to a spool (not shown) which, in turn, is adapted for rotation by motor assembly 121. In one mode, motor assembly 121 can rotate the spool so as to wind wire 127 therearound, thereby moving support 105 up along the track towards its raised position (FIG. 8). In another mode, motor assembly 121 can rotate the spool so as to unwind, and thus extend, wire 127 therefrom, thereby moving support 105 down the track towards its lowered position (FIG. 9). Rather than employing a wire to communicate the motor with the support, other embodiments contemplate the use of gear assemblies. It should be noted that other automatic shifting means, suitable for use herein, include, for example, hydraulic or pneumatic actuators. Alternatively, support 105 can be shifted by hand.

A plurality of fibers, such as optical fibers 112a–112b, are carried on support 105 for movement therewith. The fibers can be secured to the support in any suitable manner. For example, the upper end region of each fiber can be received within a respective bore extending up from the lower side of support 105. Each fiber's upper end can be held in its bore, for example, by way of frictional forces and/or by using conventional adhesives. The fibers are arranged such that the spacing between adjacent fibers substantially matches the spacing between adjacent upper-end openings of manifold 101, allowing insertion of one fiber per channel as support 105 is moved towards its lowered position. In a typical arrangement, the fibers will be disposed in a regular array.

The diameter of the fibers, extending from support 105, as well as the interior dimensions of the capillary-size regions of the channels, can be like that set out for any of the previous embodiments. In an exemplary arrangement, the diameter of each channel is less than about 200 $\mu$m, and each channel is between about 10–100 $\mu$m larger than that of an associated fiber. In another arrangement, the interior diameter along the lower end region of each channel is substantially the same as that of an associated fiber.

Upon moving support 105 to its lowered position, the lower tip of each fiber is passed through a respective channel of manifold 101 and brought to a plane adapted to be occupied by a substrate. As shown in FIG. 9, when a substrate, such as plate 22, occupies such plane, the fiber tips abut the substrate's surface at this position. In this way, each fiber can transfer an aliquot of a liquid reagent held in its respective channel to the surface of the substrate. It should be noted that the lower-end opening array of manifold 101 defines the array of spots formed on substrate 22.

As best viewed in FIG. 8, the fibers extending from support 105 are not all of the same length. Rather, they are cut such that upon being lowered through their respective channels they will contact an underlying substrate at roughly the same time, or within a short time of one another. Appropriate fiber lengths can be established by passing the fibers through the channels, and then cutting each fiber at its region intersecting the plane adapted to be occupied by the surface of a substrate. It is not critical to the successful operation of the invention that the various fibers be cut with exacting precision respective to the substrate plane, since variations in the length of fiber extending between its associated channel end and its point of contact on the substrate can be accommodated by fiber flexing.

For applications requiring formation of an array of reagent spots having the same center-to-center spacing, or pitch, between adjacent spots as between adjacent fibers of the fiber array, the pitch of both the upper- and lower-opening arrays can be made about equal. For example, in one embodiment, each of (i) the fiber array, (ii) the upper-end opening array, and (iii) the lower-end opening array all have substantially the same center-to-center spacing. For applications requiring the formation of a reagent spot array having a reduced pitch as compared to the fiber array, on the other hand, it will be advantageous to utilize a channel assembly having upper- and lower-end opening arrays that differ in pitch, as well. In one exemplary arrangement of this type, the channel lower-end opening array is provided with a center-to-center pitch that is smaller than that of the upper-end opening array. FIGS. 8 and 9 show, for example, an embodiment wherein the pitch of the lower-end opening array is substantially smaller than that of the upper-end opening array. For example, the center-to-center pitch of the lower-end opening array can be between about ½ to ¼ that of the upper-end opening array. In one particular embodiment, the center-to-center spacing of the lower-end opening array is about ⅓ that of the upper-end opening array.

According to one embodiment, a plurality of substrates are sequentially shuttled under the spotting head. For example, a conveyor can carry a number of tandemly-arranged substrates along a transport pathway passing under a manifold. The channels of the manifold can hold a single type of liquid reagent, or multiple types of liquid reagents. Upon positioning a selected substrate beneath the manifold, the conveyor can pause. At this point, the fibers can be shifted between their raised and lowered positions to lay down an array of spots on the substrate. If desired, such shifting can be repeated one or more times to transfer additional liquid to the substrate. Such additional liquid can be placed at the already-laid spots, or, upon incrementally moving the substrate laterally under the manifold, at previously unspotted regions of the substrate. The just-spotted substrate can then be moved out from under the manifold and a new, upstream substrate can be moved into position for spotting. If desired, several spotting heads can be situated at respective positions along the transport pathway. In one embodiment, a conveyor shuttles one or more substrates along a transport pathway extending under several spotting heads that are disposed sequentially along the transport pathway, at positions that are laterally offset from one another. This arrangement can provide a very compact interleaving of spots on a given substrate, even though the spots laid by any one spotting head have a wider spacing.

Changeover from one set of liquid reagents to a different set, or replacement of an emptied manifold with a loaded one, can be accomplished in a quick and efficient manner. For example, an operator or robot can simply remove the present manifold and insert another in its place. In this regard, the manifold can be configured to removably snap-lock into the frame. Where one manifold holding a first set of liquid reagents is swapped for another manifold holding a second, different set of reagents, the fiber array can be readily changed as well. To this end, the fiber support can also be constructed to removably snap-fit into the frame.

Refilling low or emptied channels of the manifold can also be readily accomplished. In this regard, the upper-end openings of the channels can be dimensioned large enough (e.g., >3 mm diameter) to permit ready access to conventional means of fluid loading, such as pipettes or syringes.

In one embodiment, both the manifold and the fiber support are constructed of relatively inexpensive materials, e.g., plastics, metal or glass, using conventional tooling and/or molding procedures. By keeping the component cost low, it can be cost-effective to throw away the fiber support (with the fibers) and/or the manifold when a new liquid reagent set is introduced. Disposing of one or both of these components, rather than cleaning and re-using them, eliminates a potential source of contamination. Furthermore, utilization of disposable components helps avoid the time, equipment, and labor costs associated with cleaning/drying efforts. In contrast, most conventional spotting systems, such as quill, ink-jet, or pin, must be cleaned each time a new fluid is deposited.

The above-described spotting devices and methods provide a relatively low-energy approach to liquid deposition. For example, the spotting head can employ a highly parallel approach to lay many spots (e.g., hundreds or thousands) per second. Notably, the process of laying any single spot is a relatively slow process. For example, each individual fiber might lay only one or a few spots per second. Consequently, problems associated with very energetic spot deposition such as splattering and misdirected ejection (satellites), and contamination resulting therefrom, are avoided by the present invention.

The spotting devices described herein offer reduced reagent loss as compared to most conventional deposition systems. According to the present invention, liquids that are deposited onto a substrate are directly transferred from a tube or channel onto the surface of a substrate without the use intermediate containers. It should be appreciated that intermediate containers typically waste fluid because of residues and films that are unavoidably left behind. For applications requiring very small amounts of fluid (e.g., a micro-liter or less), intermediate containers such as reservoirs in ink-jets or the split in a quill can waste an unacceptable amount of fluid.

Still a further aspect of the present invention provides a method and apparatus for dispensing a liquid reagent into a well or depression formed, for example, in a tray or plate. With reference to FIGS. 10A to 10E, a protrusion, such as a spike 217, extends upwardly from the bottom of a well 219 of a multi-well tray 222. A liquid container, such as an elongate tube 216, holds a liquid 218 for dispensing. Tube 216 is adapted to hold the liquid by capillary or surface tension forces. As shown in FIG. 10A to 10B, a meniscus 218*a* can form at the lower region of tube 216. Liquid 218 is dispensed by shifting tube 216 toward well 219 until spike 217 pierces meniscus 218*a*. The spike, which preferably has a wettable surface, draws liquid from the tube into the well.

FIG. 11 shows an automated system for simultaneously delivering one or more liquid reagents into a plurality of wells of a plate or tray. The system includes a manifold or channel assembly 301, similar to that described above with respect to FIGS. 8 and 9, adapted for shifting between raised and lowered positions over a substrate, such as multi-well tray 322. Manifold 301 includes a plurality of channels, such as 314*a* and 314*b*, each having a lower-end region substantially like the interior of tube 216 of FIGS. 10A to 10E. Shifting means are operable to shift manifold 301 between its raised and lowered positions. In the embodiment of FIG. 11, for example, a support 305 is configured to releasably engage an upper region of manifold 301. Support 305, in turn, is adapted to ride along a pair of parallel rails 309*a*, 309*b* provided on a frame assembly 307. A motor 321, controller 323, and power supply 325 are operable to move support 305, and thus manifold 301, up and down along rails 309*a*, 309*b* via wire 327. Although not visible in FIG. 11, each well of tray 322 includes a protrusion, such as a spike, extending upwardly from its floor. The spikes are adapted to extract liquid reagent from respective channels when manifold 301 is shifted towards its lowered position in a fashion substantially as shown in FIGS. 10A–10E.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

What is claimed is:

1. An apparatus for producing an array of liquid-reagent spots on a substrate, comprising:

a manifold having a plurality of capillary channels, each adapted to hold a selected liquid, said channels having opposite upper-end and lower-end openings, and inner diameters which decrease on progressing from the upper- to the lower-end openings, with said lower openings forming said array, a support movable between raised and lowered positions with respect to said manifold, and a plurality of fibers carried on said support for movement therewith, each fiber being adapted to move longitudinally within an associated channel, as the support is moved between its raised and lowered positions, with movement of the fibers from their raised to lowered positions being effective to deposit a selected volume of liquid from each channel in the manifold.

2. The apparatus of claim 1, wherein the spacing between adjacent upper-end openings is greater than that between adjacent lower-end openings.

3. The apparatus of claim 1, which further includes shifting means operatively connected to the support for shifting the same between its raised and lowered positions.

4. The apparatus of claim 1, wherein the diameter of the channels at their lower ends is less than about 200 $\mu$m, and from about 10 to about 100 $\mu$m larger than that of the associated fiber.

5. The apparatus of claim 4, wherein the fibers are adapted to contact such a substrate, with the support in its lowered position, and variations in the length of fiber extending between its associated channel end and its point of contact on the substrate is accommodated by fiber flexing.

6. The apparatus of claim 1, wherein each channel has a substantially uniform diameter extending along a lower end region that terminates at the channel's lower end, the diameter of each channel end region is substantially the same as that of the associated fiber, and the fiber's end, with such in its raised position, is disposed above the channel end region, such that shifting of the fiber from its raised to its lowered position is effective to expel from the channel the volume of liquid contained in said channel end region.

* * * * *